United States Patent [19]

Christiansen

[11] 4,137,245

[45] Jan. 30, 1979

[54] NITROGENOUS CONDENSATION PRODUCTS

[75] Inventor: Arvid Christiansen, North Arlington, N.J.

[73] Assignee: The Miranol Chemical Company, Inc., Irvington, N.J.

[21] Appl. No.: 798,279

[22] Filed: May 19, 1977

Related U.S. Application Data

[62] Division of Ser. No. 598,092, Jul. 22, 1975, Pat. No. 4,044,034.

[51] Int. Cl.$^2$ ............................................. C09F 5/00
[52] U.S. Cl. ............................... 260/404.5; 560/196; 548/352
[58] Field of Search ............... 260/404.5 R, 404.5 PA, 260/404.5 EO; 560/196; 548/352

[56] References Cited

U.S. PATENT DOCUMENTS

| 3,262,951 | 7/1966 | Katz | 260/404.5 |
| 3,816,378 | 6/1974 | Schmadel | 560/196 |

OTHER PUBLICATIONS

Chemical Abstracts 60: P10933d.

*Primary Examiner*—John Niebling
*Attorney, Agent, or Firm*—Ladas, Parry, Von Gehr, Goldsmith & Deschamps

[57] ABSTRACT

Nitrogenous condensation products and hydrolysis products thereof are provided wherein the condensate of a fatty acid and diamine is reacted with an unsaturated dicarboxylic acid or a partial ester thereof; optionally the product of such a reaction or a similar product obtained from an unsaturated monocarboxylic acid is further reacted with a halocarboxylic acid. The unhydrolyzed products can be formulated as imidazolines.

6 Claims, No Drawings

NITROGENOUS CONDENSATION PRODUCTS

This is a division of application Ser. No. 598,092 filed July 22, 1975, now U.S. Pat. No. 4,044,034.

FIELD OF THE INVENTION

This invention relates to condensation products of fatty acids and diamines also known as imidazoline derivatives and hydrolysis products thereof and particularly to the production thereof and to products having surfactant properties. The imidazoline derivatives are 2-imidazolines but for convenience hereinafter the term imidazoline is used for materials.

BACKGROUND OF THE INVENTION

Various imidazoline derivatives particularly those having amphoteric properties have been suggested and used in surfactant compositions. Thus, in U.S. Pat. No. 3,408,361 of Hans S. Mannheimer dated October 29, 1968, certain hydroxyethyl imidazolines are described. Other art in United States Patent is U.S. Pat. Nos. 2,155,877 to Waldmann (1939) and 2,267,965 to Wilson (1941) and U.S. Pat. No. 2,520,102 to Tryon (1950). These imidazoline products are obtained by reacting a diamine for example, one of the formula $NH_2C_2H_4NHR_a$—OH and a fatty acid of generic formula R—COOH wherein R is 5 to 25 carbon atoms and is alkyl or alkenyl, $R_a$ is $R_1(OR_1)_n$ in which $R_1$ is an alkylene of 2 to 4 carbon atoms and n is 0 to 4. The amines used in preparing the condensates have primary amino groups and a second primary or a secondary amino group in 1:2 position to each other. In the aforesaid United States Patent the diamine and fatty acid are reacted to remove water of reaction. When only one mole of water is removed an open-chain product is obtained, considered to be for example, in the instance where n is 0 of the formula:

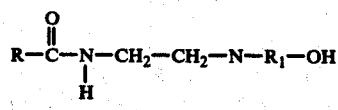

which can be described as an amide. If more than one mole of water is removed the imidazoline ring structure is considered to be formed giving for example, in the instance where n is 0 product of formula:

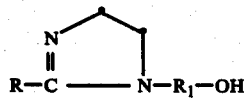

For convenience the imidazoline ring structure in this specification if formalized: the correct formula is:

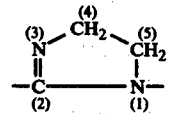

The imidazoline can be converted to the open-chain structure by hydrolysis and in the art these open-chain products whether originally or by hydrolysis are regarded from many aspects as having the equivalent properties to the imidazolines although not demonstrating the closed ring structure. Moreover, the initial condensation product generally contains a mixture of open-chain and ring closed (imidazoline) products.

The preparation of an imidazoline substituted in the 2-position by a long chain aliphatic hydrocarbon radical is well described in the literature and is readily carried out by reaction described above between a carboxylic acid and a polyamine containing at least one primary amino group and at least one secondary amino group. Since to obtain the product of the present invention it is necessary to obtain at some time the hydroxy group on a 1-aliphatic hydrocarbon substituent usually the hydroxy ethyl type amine is desirable but a hydroxy group can be substituted on to the appropriate 1-alkylene sidechain by those methods normal in the art.

A nitrogen on the ring has been further reacted with an alkylating agent, for example, sodium chloroacetate, (U.S. Pat. No. 2,528,378 of Mannheimer 1950) to provide structures considered as having the formula:

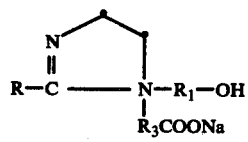

wherein R and $R_1$ are as defined above and $R_3$ is an alkylene group of 1 to 3 carbon atoms, for example, methylene.

When in hydrolyzed or open chain form such structures could be regarded as having the structure:

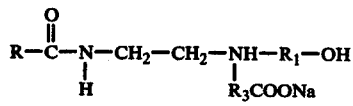

Correspondingly, the imidazolines may be reacted with a monocarboxylic unsaturated acid or ester (United Kingdom Pat. No. 1,078,101 of Arndt, 1967 and U.S. Pat. No. 3,555,041 of Katz) to provide structures considered as having the formula:

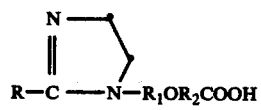

wherein R and $R_1$ are as defined above and $R_2$ is alkylene of 2 to 4 carbon atoms.

When in hydrolyzed or open chain form such structures could be regarded as having the structure:

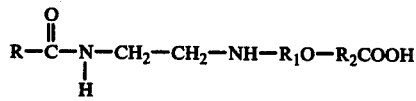

As mentioned, in U.S. Pat. No. 2,528,378 there is described the preparation of a condensate of a diamine with a fatty acid which is then further reacted with a monohalo monocarboxylic acid particularly a metal salt thereof.

Such products have been found to demonstrate various surfactant or detergent properties and to be useful in products requiring good foaming properties and particularly those requiring fine bubble structure with good stability, for example, shampoo compositions. Nevertheless, despite the improvements obtained there is still a need for improvement in foam structure and stability of compositions particularly shampoo compositions. The present invention has as its objects imidazolines and the related open-chain structures which products can also be described as modified condensation products of diamines and fatty acids, having improved properties for use in detergent or surfactant compositions, for example, shampoos.

SUMMARY OF THE INVENTION

The present invention provides certain nitrogenous compounds of the formula:

$$R-A-R_1-O(R_1-O)_n-Ac$$

wherein R is alkyl or alkenyl aliphatic group of 5 to 25 carbon atoms;
each $R_1$ is alkylene of 2 to 4 carbon atoms and may be the same or different;
n is 0 to 4;
A is selected from the group consisting of:

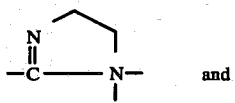

and

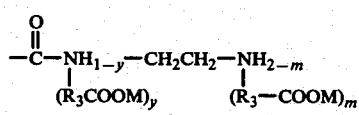

$R_3COOM$ is the residue of monocarboxylic acid of 2 to 5 carbon atoms $-C_xH_{2x}-COOM$ wherein x is 1 to 4;
m is from 0 to 2;
y is 0 or 1;
M is H or a cation, for example, an alkali metal such as sodium or potassium or an organic base;
Ac is selected from the group consisting of a residue of an α,β-unsaturated dicarboxylic acid of 4 to 5 carbon atoms, a partial ester thereof, a salt of said acid or partial esters and $-R_2COOM$;
$-R_2COOM$ is the residue of an α,β-unsaturated monocarboxylic acid wherein $R_2$ is alkylene of 2 to 4 carbon atoms, providing that if Ac is $-R_2COOM$ then m is greater than 0.
Preferably if Ac is the residue of a monocarboxylic acid $-R_2COOM$ then y+m is greater than 1.
Generally in these products a preferred fatty acid used in preparing the condensate is lauric acid giving R as undecyl.
Preferably the compounds are of the formula:

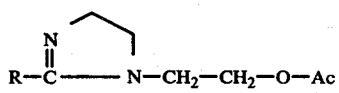

wherein R is alkyl of 5 to 25 carbons and Ac is a residue of unsaturated dicarboxylic acid of 4 to 5 carbons, and particularly preferred as Ac are $$-\underset{CH_2-COOH}{\underset{|}{CH}}-COOH \quad or \quad -\underset{CH-COOH}{\underset{|}{CH}}-COOR_4;$$

wherein $R_4$ is alkyl of 1 to 6 carbons.
A preferred hydrolyzed form is of formula:

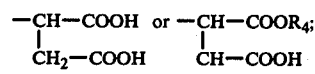
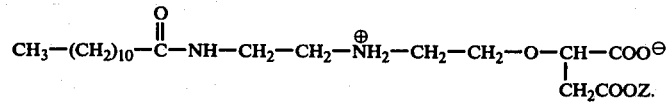

Another preferred product is:

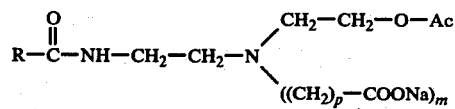

wherein R is alkyl of 5 to 25 carbons, m is from 1 to 2 and Ac is a residue of an unsaturated mono- or dicarboxylic acid or half ester thereof and particularly one in which R is undecyl, p is 1 or 2, m is from 1 to 1.3, and Ac is

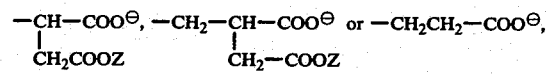

wherein Z is selected from the group consisting of M, H and $R_4$ which is alkyl of 1 to 6 carbons preferably 1 to 4, and M is a cation.

From another aspect the invention comprises a modified condensation product of a diamine which is of formula $NH_2CH_2CH_2NHR_a-OH$ wherein $R_a$ is as hereinbefore defined and preferably is $R_1$ which is alkylene of 2 to 4 carbon atoms with a fatty acid of formula R—COOH wherein R is as hereinbefore defined which reaction product has from 1 to 2 mols of water removed during condensation. Said condensation product of the invention is the basic condensation product which is modified by condensation with an unsaturated dicarboxylic acid or a partial ester thereof. The resulting product can be further modified by alkylation to add the residue of an alkanoic acid. Instead of a dicarboxylic acid the basic condensation product can also be modified by condensation with a monocarboxylic unsaturated acid, but such a reaction product must be further alkylated to add the residue of an alkanoic acid.

These compounds can be prepared from a condensation imidazoline product as previously described in this specification.

DETAILED DESCRIPTION OF THE INVENTION

Condensates and the preparation thereof are described in detail in the art for example in U.S. Pat. No. 3,408,361 to Mannheimer, although the preparation of the starting materials of this invention is not confined to such method and any technically appropriate method for the preparation of such starting materials can be employed. Essentially, one method for the preparation of the starting materials is to condense a diamine and a fatty acid. The fatty acids can be replaced by esters, amides, anhydrides or halides. When one mole of water is removed during such condensation the basic product will then be considered to be of Formula I. More usually, more than one mole of water is removed and the product will then be considered to contain an appropriate amount of imidazoline ring structure of Formula II. Hereinafter the term condensate is applied to the immediate product of such condensation of fatty acid and amine with up to 2 mols of water being removed. As already indicated a hydroxy amine can be employed or the hydroxy group can be substituted in the hydrocarbon side chain at the 1-position after formation of the condensation product by techniques customary in the art. The preferred method, however, is the use of a hydroxy alkyl alkylene polyamine for reaction with the fatty acid.

The nature of the fatty acid residue is preferably a residue of a fatty acid of 6 to 26 carbon atoms, preferably 8 to 22 carbon atoms. Typical acids are coconut, lauric oleic, tall oil fatty acids, stearic, sebacic, n-valeric, isovaleric, caproic, heptoic, caprylic, pelargoni, capric, undecylic, tridecylic, myristic, pentadyclic, palmitic, margaric, octadecyclic, nonadecyclic, linoleic, erucic acid, cyclohexyl acetic and arachidic. Naphthenic and long chain fatty acids having an aromatic hydrocarbon radical connected directly to the aliphatic chain may be employed while certain unsaturated analogues may be used, as can be substituted analogues, including fluorinated analogues. The presence of minor or even major amounts of impurity such as the unsaturated fatty acids for instance, is not necessarily detrimental and these can be used as the primary fatty acid. The fatty acids can also include those obtained from the oils of fats of animal, marine or vegetable origin including coconut, palm kernel and palm oil acids which contain fatty acids having at least 11 carbon atoms, also from soy bean, linseed, olive, rape seed, cotton seed, peanut and castor oil which contain large proportions of unsaturated hydroxy fatty acids. Mixtures of fatty acids can be employed. An ester can sometimes be employed, the alcohol being split off during the reaction and being removed as by distillation.

While the invention is primarily described in relation to $R_1$ as ethylene as already indicated other alkylene groups of 1 to 6 carbon atoms can be employed for example, propylene, particularly isopropylene, isobutylene, n-butylene or secondary butylene and pentylene or hexylene groups depending on the choice of amine. A preferred amine is aminoethylethanolamine which gives $R_1$ as $-CH_2-CH_2-$ and another preferred amine is aminoethylisopropanolamine. The alkylene amide adducts obtained by reacting a product wherein $R_a$ is $R_1-OH$ with up to 4 mols of an alkylene oxide e.g. ethylene oxide or propylene oxide can be employed as the initial amine for condensation with the fatty acid. Polyoxyalkylene amines prepared by other techniques can also be employed.

The present invention is exemplified by a limited number of condensates. However, in view of the extensive art on said condensates which are recognized as having equivalent properties it will readily be recognized by those skilled in the art that any given fatty acid or diamine as exemplified can be replaced and results obtained which are within the normal range of properties useable in the present invention.

The condensate whether regarded as pure imidazoline or as a mixture of imidazoline and open-chain product or simply as a condensate is then reacted to provide the products of the invention. The basic condensate is hereinafter referred to as the condensate.

Generally, the condensate is a mass which although solid at room temperatures can be melted without decomposition often at temperatures below 100° C. The initial reaction product of the invention with unsaturated carboxylic acid can be obtained simply by adding carboxylic acid to molten condensate. Preferably, addition takes place over a period sufficient to allow even reaction without unnecessary concentration of the acid at any given time. The exact rate of addition of the acid to the molten condensate is simply a matter of technical expertise. The reaction conditions for the reaction between unsaturated acid and condensation product can vary widely providing that the conditions are sufficiently vigorous to initiate the reaction between the reactants. A temperature range of approximately 20° C. to 100° C. is available, although at too high a temperature one may have degradation of some products. The unsaturated acid or ester should be added at such rate that the molar concentration in the reacting process at any given time is such as to minimize polymerization and particularly self polymerization. The reaction can be carried out in solvents or simply by addition of the unsaturated acid to the molten mass of condensation product. In that the reaction can be regarded essentially as a reaction of a hydroxy group with an unsaturated carboxylic acid, those techniques available generally for such reactions can be employed, having regard to the physical properties of the reactants.

The unsaturated dicarboxylic acids must have two carboxylic groups on adjacent carbon atoms and either between these two carbons or immediately adjacent to them an unsaturated grouping. The preferred acids are those of 4 to 5 carbon atoms as exemplified by maleic, fumaric, itaconic.

The unsaturated dicarboxylic acid residues which can be employed in the final product include the partial esters thereof up to the half ester. A partial ester can preferably be employed having from 25 to 50% esterification. By 25% esterification is meant that in a given amount of acid up to 25% of the acid groups present are esterified and 50% esterification would mean that the half ester was formed. A preferred ester is the half-ester or "50%" partial ester. While preferably in most instances the partial ester would be reacted with the condensate an alternative route would be to react the free acid and then esterify partially up to 50% the carboxylic groups in the product. Various conventional esterification techniques for use in this reaction are readily available to those skilled in the art. An alternative technique is to react a full ester and then hydrolyze either to a partial ester (50% or below) or completely to free acid.

The partial esters of the dicarboxylic acids include methyl esters, ethyl esters and other lower alkyl esters of up to 6 carbons, e.g., hexyl ester.

When the resulting product is prepared substantially from unhydrolyzed material it can be transformed into a hydrolyzed product by forming an aqueous solution and hydrolyzing preferably in the presence of a base for instance sodium hydroxide, potassium carbonate, ammonia, monoethylamine, diethylamine, thriethylamine and mono- di- or tri- ethanolamine.

The preferred base is sodium hydroxide. After hydrolysis it is generally desirable to neutralize the base when used by addition of an acid, particularly an inorganic strong acid such as hydrochloric acid. However, even without hydrolysis the reaction product of condensate and a dicarboxylic acid or an ester thereof is a commercially significant product. In neutralizing, various acids can be employed including hydrochloric acid, sulfuric acid, nitric acid, although hydrochloric acid is preferred. In the final product M, if not hydrogen, can be one of the cations used customarily in the art of surfactant amphoterics but is customarily an alkali metal, for example, sodium or potassium, but organic bases can also be employed.

In this hydrolysis as indeed in all the hydrolysis reactions described herein fission of the imidazoline structure is most probably between the 2-Carbon and 1-Nitrogen but can also be speculated as being at least partially between the 2-Carbon and 3-Nitrogen.

In many circumstances a final commercial product is obtained by addition of water to form a solution. The pH of such solutions will generally be from 4 to 10 but is usually slightly acid particularly for unhydrolyzed materials to minimize spontaneous hydrolysis.

The condensation product can be reacted with a compound which generates a residue of an unsaturated monocarboxylic acid of 3 to 5 carbons for example acrylic acid or methyl acrylate. The reaction can be effected by simple addition of, for instance, the acrylate at a temperature of from 30° to 100° C. Thus, the acrylate can be added over a period of say one to three hours followed by heating for from to 24 hours at from 50° to 110° C. The final process can be under vacuum to remove any unreacted acrylate. The product can then be treated with water and caustic soda to hydrolyze and neutralize the acid groups. Acrylate monomers which are suitable for reaction may be acrylic acid, methacrylic acid, methyl acrylate, ethyl acrylate, methyl methacrylate, isopropylacrylate, acrylamide and/or acrylonitrile. The reaction is found to go to substantial completion under specific conditions and no particular catalyst is required since it appears that the basicity of the tertiary nitrogen atoms is sufficient to self-catalyze the acrylic monomer adduct reaction. Adduct formation can be obtained in some instances by simple addition of monomer acrylate to condensate at temperatures near room temperature although usually it is desirable to increase the temperature to 60° C.–100° C. with removal of unreacted monomer under vacuum. When other than free acids are employed (e.g., acrylamide or acrylonitrile) a specific hydrolysis step will be required to produce the free acid. For example boiling in aqueous system in the presence of a base at 90°–100° C. until ammonia is completely removed (or alcohol for esters).

There can be an additional alkylating reaction e.g. with a haloalkanoic acid, for instance sodium chloracetate. Preferably this reaction is effected with hydrolyzed products. Since this reaction involves alkylation and possible quaternization of one of the nitrogen atoms the reaction is primarily available with open-chain compounds, i.e., hydrolysates rather than the imidazolines. When the original reaction of condensate with the unsaturated carboxylic acid is with a monocarboxylic acid then this additional step is a necessary feature of the invention. The alkylation can be carried out in a single stage in which both hydrolysis and reaction with a haloalkanoic acid is simultaneous or there can be an hydrolysis of the product followed by the reaction with an alkylating agent such as an haloalkanoic acid.

A reaction with three mols of alkylating agent is visualised as shown in the Formulae substituting onto the 1-position but substitution at the 3-position may be possible with consequent effect on the structure of the hydrolyzed products. However even if a 3-position substitution is effected hydrolysis may result in isomerising to form the same hydrolysis products as the 1-substitution.

A reaction with haloalkanoic acid can be carried out under a variety of conditions either in the presence of a solvent or more usually in the presence of an aqueous system. For instance the sodium haloacetate can be added to the hydrolyzed system with heating and with or without the addition of a base.

Thus, the condensate reaction product with the unsaturated carboxylic acid can be reacted with a monohalocarboxylic acid in the presence of caustic soda (sodium hydroxide in aqueous solution). In a preferred form one mol of the reaction mass is added to an aqueous solution containing one mol of the monohalo carboxylic acid and from 2.2 to 2.5 mols of caustic soda and the mix is then heated to a temperature of approximately 95° C. until there is no change in pH. The pH normally drops from about 13 to approximately 8. Additional caustic soda is added to increase the sum of caustic soda to approximately 3 mols and the mass is maintained until there is a sparkling clear solution when adjusted to a pH of from 9 to 10.

Another reaction is as described in U.S. Pat. No. 2,407,645 to Bersworth (1946) wherein the hydrolyzed condensate reaction product with unsaturated acid is reacted with an alkali metal cyanide and a formaldehyde-yielding substance, then hydrolysed to drive off ammonia. Such a reaction can be used to add 2 mols of alkanoic acid and then one could react with haloalkanoic acid to add a further carboxyalkyl group.

Typical haloalkanoic acids are the sodium or potassium salts of chloracetic acid, and $\alpha$- or $\beta$-chloropropionic acids.

For reaction products with dicarboxylic acids up to three mols of alkanoic acid residue can be substituted preferably 0–2. For reaction products of monocarboxylic acids there must be some alkylation and again up to three mols can be added but a preferred range is 1–2 mols.

In another method of reacting one can react the basic condensate with the unsaturated acid then simply add water and alkali metal haloalkanoate. Thereafter add alkali (e.g., sodium hydroxide) and heat to 100° C. for say one hour.

The final products are generally obtained in the form of aqueous solution and may contain residues of reactants employed in preparing the final product. The adduct of unsaturated acid and condensation product can be a commercial product as such without addition of water. As is customary in this art the pure product is often not recovered from the aqueous solution and determination of the structure of the product is an educated estimate based on the chemistry involved and the properties of the solution or adduct.

These products have amphoteric properties wherein the unreacted condensates are cationic in nature, therefore a test for completion of reaction is the extent to which the final product forms clear aqueous solutions at high and low pH values.

The products of the invention, particularly when in aqueous solution, are of value in various surfactant compositions and particularly in emulsions, cosmetics, detergents and can be combined with other surfactants. Solutions of the products of the invention can comprise an aqueous solution with as major organic components, the product of the invention. The organic content of such a solution can measure from 20 to 90% by weight thereof for example 30 to 70%. The solutions represent finished products of commerce although they are frequently later combined by customers with other materials to provide compositions for different purposes especially in the field of cosmetic compositions.

The products of the invention are particularly valuable in shampoos in assisting in the rendering of conditioning agents particularly for instance, polycationic cellulose derivatives, compatable with other surfactants for instance sulfates. Moreover, certain of the products of the invention at the same time can assist in improving the skin and hair conditioning properties of cosmetic products. The products of the invention are generally water-soluble as already indicated but some have the advantage of limited solubility in dilute solutions.

The products of the invention as already mentioned can be incorporated in cosmetic preparations where it is desired to emulsify an aqueous phase and the normally lipophilic phase such as mineral oil, which may be the continuous one. The compounds and their organic sulfate complexes are generally non-antagonistic toward most cosmetic ingredients.

Certain of these products can form complexes which may be complex salts with organic sulfates e.g. sodium lauryl sulphate, sodium polyoxyethylene (3.5) lauryl sulfates, sodium polyoxyethylene (3) tridecyl sulfate.

The compounds are useful as hair and skin conditioners, hair rinses, creams, fabric softeners, laundry applications and cationic emulsifiers and can be generally highly efficient hair and skin conditioners generally without markedly reducing foaming as do conventional conditioners when used in solutions. The ratio of compound employed to water can be from 1.00 to 99.9% of the organic compound. The compounds can also be used in textiles to improve textile finishing.

One of the most active areas in shampoo research is creating a conditioning property into the shampoo. It would be desirable if the necessity of a post-shampoo cream rinse could be eliminated. A most effective, and widely used conditioning agent is a polycationic cellulose derivative, for example, one made by reacting cellulose derivatives with epichlorhydrin, then condensing with trimethylamine (commercially available as "Polymer JR" which is a Trademark of Union Carbide Corp). One of the problems in using this type of resin (usually at a level of about one percent cof the shampoo formula) is that it is incompatible with many compounds used in shampoos which are anionic.

The products of this invention tend to couple and compatibilize such resins and organic sulfates. It is a valuable aspect of the products employing the residues of dicarboxylic acids and particularly partial esters of such unsaturated dicarboxylic acids that they act as coupling agents in shampoos containing such resins and organic sulfates. The shampoos have all the desirable properties of this general type of product, foaming and conditioning very well.

Adducts of esters of maleic acid, hydrolyzed and unhydrolyzed, couple organic sulfates and Polymer JR, to form clear or nearly clear solutions, whereas adducts prepared from maleic acid and itaconic acid form homogeneous but cloudy or pearlescent mixtures.

Adducts prepared from esters of maleic acid also seem to foam better than the other products, when combined into shampoo formulations containing both organic sulfates and Polymer JR Resin.

Generally products which are not alkylated may have superior conditioning properties to alkylated products but the latter are superior in foaming and lathering.

The invention will now be illustrated by examples:

EXAMPLE I

PREPARATION OF CONDENSATE

Lauric acid aminoethylethanolamine condensate is prepared as described in Example 1 of U.S. Pat. No. 3,408,361 by charging aminoethylethanolamine to a vessel containing lauric acid heated at about 100° C. and a mole ratio of said fatty acid to diamine of from 1 to 1.096.

This product may be considered as consisting substantially of a product believed to be of the formula:

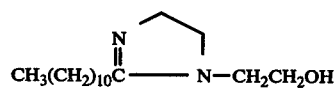

Having regard to the particular method used for making this product it was considered to have primarily the aforesaid structure but it will be appreciated that certain small proportions of amide be present and different methods of preparation might give greater amounts of amide of the structure:

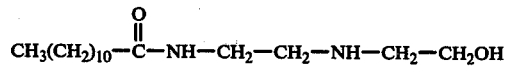

The approximate molecular weight of the condensate starting material of the present invention is 268.

PREPARATION OF REACTION PRODUCT OF INVENTION

Lauric Condensate plus Itaconic Acid

A glass flask equipped with stirrer and thermometer was charged with 1185 g. (approx. 4.4 moles) molten condensate. Over a period of two hours, 664 g. (approx. 5.1 moles) itaconic acid was slowly added to the mass, starting at 55° C. and ending at 71° C. Temperature was maintained at 69° to 72° C., for 19 hours when 1849 g. of water was added. The resulting thin, clear, amber colored product, cooled to room temperature had a pH of 4.3.

A 40% aqueous solution of this material, neutralized to pH 4.3 to 7 with 50% NaOH solution, vigorously massaged onto the scalp and hair after shampooing, foamed copiously, left the hair, after rinsing, relatively static- and snarl-free, with a smooth, soft feel.

The active content of this product is believed generally to conform to the formula:

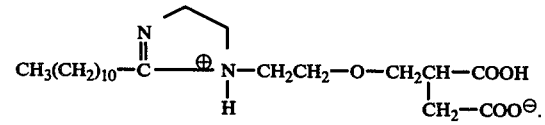

EXAMPLE II

Lauric Condensate plus Itaconic Acid, Hydrolyzed

A glass flask equipped with stirrer, thermometer and reflux condenser was charged with 1849 g. (approx. 4.4 moles) of the product of Example I just prior to addition of water. With stirring, the mass was heated to 70° C. and 1849 g. of water and 500 g. of 50% aqueous NaOH solution were added, lowering the temperature to 62° C. It was heated to 70° C. Fifty percent aqueous sodium hydroxide solution was added to the stirred mass at 70° to 72° C., over a three hour period, keeping the pH, measured at 30° C., at 9.0 to 9.4. A total of 668 g. of 50% aqueous sodium hydroxide solution was used. The mass was cooled and 265 g. of 31.5% hydrochloric acid solution was used to neutralize the product to pH 7.8. The final product was clear and viscous.

A 40% aqueous solution of this material, neutralized to pH 4 to 7 with hydrochloric acid, vigorously massaged onto the scalp and hair after shampooing, foamed copiously, left the hair, after rinsing, relatively static- and snarl-free, with a smooth, soft feel.

The active content of this product is believed to conform to the following formula or one of its isomers:

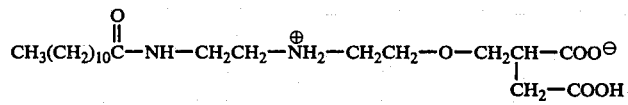

EXAMPLE III

Lauric Condensate plus Maleic Acid

A glass flask equipped with stirrer and was charged with 474 g. (approx. 1.77 moles) molten condensate of Example I. Over a period of two hours, 237 g. (2.04 moles) maleic acid was slowly added to the mass, starting at 65° C. and ending at 73° C. The mass was maintained at 66° to 74° C., for 19½ hours, when 711 g. of water was added. The resulting thin, clear, amber colored product, cooled to room temperature, had a pH of 2.98.

A 40% aqueous solution of this material, neutralized to pH 4 to 7 with 50% NaOH solution, vigorously massaged onto the scalp and hair after shampooing, foamed copiously, left the hair, after rinsing, relatively static- and snarl-free, with a smooth, soft feel.

The active content of this product is believed to conform to the formula:

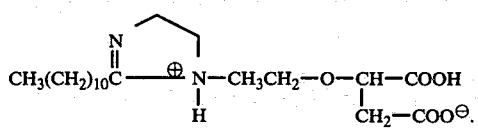

EXAMPLE IV

Lauric Condensate plus Maleic Acid, Hydrolyzed

Example III was repeated using 1232 g. (approx. 4.6 moles) condensate of Example I, 616 g. (5.31 moles) maleic acid and 1849 g. of water. The heating period was 16 hours at 72° to 85° C. After the water had been added, 555 g. of 50% sodium hydroxide solution was added. The mass was heated six hours at 68° to 72° C., as an additional 100 g. of 50% sodium hydroxide solution was slowly added to maintain the pH at 9.0 to 9.2.

1535 g. of this final reaction mass was neutralized to pH 7.58 with 81.0 g. 31.5% HCl solution.

A 40% aqueous solution of this material, neutralized to pH 4 to 7 with 50% NaOH solution, vigorously massaged onto the scalp and hair after shampooing, foamed copiously, left the hair, after rinsing, relatively static and anarl-free, with a smooth, soft feel.

The active content of this product is thought generally to conform to the following formula or one of its isomers:

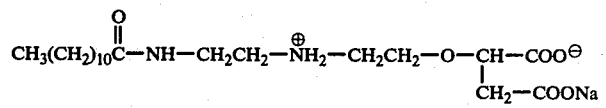

EXAMPLE V

Lauric Condensate plus Maleic Acid plus Sodium Monochloroacetate

A glass flask equipped with stirrer, thermometer and condenser was charged with 2772 g. (approx. 2.93 moles) of the reaction product of Example IV prior to having been neutralized with HCl. To this was added 512 g. (approx. 4.39 moles) sodium monochloroacetate over a 20 minute period between 50° and 53° C. The mass was heated to 97° C., over a period of 1½ hours, while 512 g. water slowly was added and 50% sodium hydroxide solution was added to maintain the pH of the reaction mass at 8.6 to 9.4 (measured at 30° C.). Stirring with heating at 97° to 100° C., was continued for an additional 2¼ hours, maintaining the pH (30° C.) at 8.7 to 9.4. In all a total of 400 g. of 50% sodium hydroxide solution was used. With cooling, an additional 1000 g. water was added to yield a thin, clear, light amber colored product having a pH of 9.42, non-volatile content of 41.1% and a sodium chloride content of 5.02%.

A 40% aqueous solution of this material, neutralized to pH 4 to 7 with HCl gave a good head of foam when used as a hair shampoo, leaving the hair soft and manageable. It was practically non-irritating to the eyes of rabbits as tested according to the method of Draize.

The active content of this product is believed generally to conform to the following formula or one of its isomers:

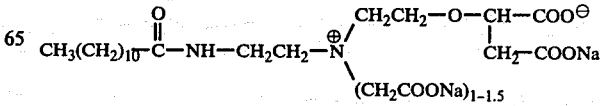

EXAMPLE VI

Lauric Condensate plus Acrylic Acid plus Sodium Monochloroacetate

A glass flask equipped with stirrer, thermometer and reflux condenser was charged with 1400 g. (5.22 moles) condensate of Example I. With stirring, 434 g. (6.03 moles) acrylic acid was added over a 4 hr. 10 min. period at between 65° and 70° C. The mass was stirred and maintained at 57° to 77° C., for 21½ hours, after which 1834 g. water was added.

To 680 g. (approx. 0.97 moles) of this reaction material was added 174.8 g. (1.5 moles) sodium monochloroacetate over a 20 minute period, from 50° to 60° C. The mass was heated to 98° C., over a period of 1¾ hours, while 50% sodium hydroxide solution was added to maintain the pH of the reaction mass at 9.0 to 9.6 (measured at 30° C.). Stirring with heating at 98° C., was continued for an additional 3¼ hours, maintaining the pH (30° C.) at 9.0 to 9.3. In all a total of 194 g. of 50% sodium hydroxide solution was used. With cooling, 175 g. water was added to yield a thin, clear, light amber colored product having a pH of 9.36, non-volatile content of 49.4% and a sodium chloride content of 7.22%.

A 40% aqueous solution of this material, neutralized to pH 4 to 7 with HCl gave a good head of foam when used as a hair shampoo, leaving the hair soft and manageable. It was practically non-irritating to the eyes of rabbits as tested according to the method of Draize.

The active content of this product is thought generally to conform to the following formula or one of its isomers:

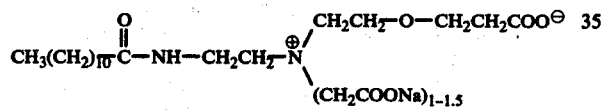

EXAMPLE VII

A condensate is prepared according to Preparation I from each of the following acids:
Run
1 Caproic acid
2 Capric acid
3 Myristic acid
4 Behenic acid
5 Oleic acid
6 Linoleic acid
7 Palmitic acid Each of the condensation products is individually reacted with:
(1) Maleic acid
(2) Itaconic acid
(3) Fumeric acid
(4) The half ethyl ester of maleic acid.

Runs 1, 3 and 7 are repeated with aminoethylisopropanolamine and each of the products is reacted separately with maleic acid.

The method employed is that of Example I in each case.

In each case a product is obtained which is soluble in water and has good foaming properties.

EXAMPLE VIII

Each of the condensation products of Runs 1 to 7 is reacted with maleic acid and hydrolyzed following the procedure of Example IV. A satisfactory product is obtained in each case in terms of foaming properties.

EXAMPLE IX

Each of the products from the reaction with maleic acid is hydrolyzed as in Example V and reacted with sodium chloroacetate using the conditions of Example V. The product is satisfactory in each case in terms of foaming properties.

EXAMPLE X

Amino ethyl ethanolamine ($NH_2C_2H_4NHC_2H_4OH$) is reacted as described in U.S. Pat. No. 2,528,378 to Mannheimer with lauric acid (Example I, references are the Examples of 2,528,378 which are hereby incorporated by reference), capric acid (Example 3), linseed fatty acid (Example 4), caproic acid (Example 5), stearic acid (Example 6), dodecyl benzoic acid (Example 7), myristic acid (Example 8). Thereafter each condensate obtained is reacted with each of the following unsaturated carboxylic acids: maleic acid, fumaric acid and with mcnoethyl maleate following the procedure of present Example I.

Each of the products when formed into solution as in Example I have satisfactory foaming properties. The condensates with lauric acid and caproic acid are reacted with acrylic acid as in Example VI and the resulting product is then reacted with in one instance sodium chloracetate and in the second instance with sodium bromopropionate following the procedure of Example VI to obtain an aqueous solution. The resulting solutions have satisfactory foaming properties.

EXAMPLE XI

Lauric Condensate plus Ethyl Maleate

A glass flask equipped with stirrer and thermometer was charged with 938 g. (approx. 3.5 moles) molten condensate. Over a period of about two hours, 616 g. (approx. 4 moles) of a 94% ethanol solution of monoethylmaleate was slowly added to the mass, starting at 60° C. and ending at 73° C. The temperature was maintained at 70° C. to 75° C., for about 22 hours. 1554 g. water was added, to yield a clear, light amber liquid having a pH of 4.1 and a solids content of 46.7%.

EXAMPLE XII

Lauric Condensate plus Ethyl Maleate, Hydrolyzed 2138 g. of the product of Example X was heated, with stirring, with 122. g 50% NaOH, to 90° C., the boiling point of the solution. A total of 300 ml. distillate was collected and replaced with water as the temperature slowly rose to 100° C. Fifty percent NaOH was added during this time to keep the pH above 9.0. A total of 339 g. of 50% NaOH was used in all. When the boiling point of 100° C. was reached, indicating essentially all the ester was hydrolyzed and the ethanol removed, and the reaction product was cooled, 300 ml. of water was added back to the reaction mass. The resulting clear, amber solution has a pH of 10.0 and a solids content of 44.3%.

EXAMPLE XIII

Lauric Condensate plus Maleic Acid Alkylated

To 10 mols of the product of Example III is added 4 mols of caustic soda, eight mols of sodium cyanide are added and 7.5 mols of formaldehyde are added. The conditions and methods of addition are as described in Example I of U.S. Pat. No. 2,407,654. Addition of sodium cyanide and formaldehyde is repeated after evolution of ammonia ceases for each batch addition. The resulting product in aqueous solution has excellent foaming properties.

EXAMPLE XIV

A number of examples of shampoos were prepared. Some typical formulations follow.

| | % by wt. | % active |
|---|---|---|
| A. Condensate of lauric acid and aminoethylethanolamine reacted with monoethylmaleate, hydrolyzed. | 22.6 | 10.0 |
| Sodium polyoxyethylene (3) tridecyl sulfate | 11.6 | 8.0 |
| Polymer JR 400, 2% aq. soln. | 50.0 | 1.0 |
| Water | 15.8 | 0 |
| | 100.0 | 19.0 |
| | neutralized to pH 6.7 with HCl. | |

This shampoo is a clear, syrupy liquid which foams very well when used as a hair shampoo. After rinsing, the hair is left with exceptional wet-comb and untangling properties.

| Product of Invention | % by weight | % active |
|---|---|---|
| B. Condensate of lauric acid and aminoethylethanolamine reacted with monoethylmaleate, unhydrolyzed. | 30.0 | 14.0 |
| C. Condensate of lauric acid and aminoethylethanolamine reacted with monoethylmaleate, hydrolyzed. | 31.6 | 14.0 |
| D. Condensate of lauric acid and aminoethylethanolamine reacted with monomethylmaleate. | 29.2 | 14.0 |
| E. Condensate of lauric acid and aminoethylethanolamine reacted with monomethylmaleate, hydrolyzed. | 29.6 | 14.0 |
| Sodium polyoxyethylene (3.5) lauryl sulfate | 20.0 | 5.0 |
| Polymer JR-400 | 1.0 | 1.0 |
| Water | q.s. | 0 |
| All neutralized by pH 6.7 with either NaOH or HCl. | | |

Results:
B. Clear, syrupy liquid with good cream rinse action and conditioning properties when used as a hair shampoo.
C. Very slightly hazy, syrupy liquid. Good wet-comb and untangling properties when used as a hair shampoo.
D. Very slightly hazy, syrupy liquid. Very good cream rinse action and wet-comb properties when used as a hair shampoo.
E. Very slightly hazy, syrupy liquid. Very good wet-combing properties when used as a hair shampoo.

| | % by wt. | % active |
|---|---|---|
| Condensate of lauric acid and aminoethylethanolamine reacted with monoisopropylmaleate. | 26.8 | 12.7 |

-continued

| | % by wt. | % active |
|---|---|---|
| Sodium polyoxyethylene (3.5) lauryl sulfate | 18.2 | 4.6 |
| Dimethylcocoamine oxide | 9.1 | 3.6 |
| Polymer JR-400 | 0.9 | 0.9 |
| Water | 45.0 | 0 |
| neutralized to pH 6.7 with NaOH | | |

This is a very slightly haze, syrupy liquid, which foams well when used as a hair shampoo.

I claim:
1. A nitrogenous compound of the formula

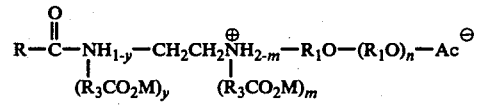

wherein $R_3CO_2M$ is the residue of a monocarboxylic acid of 2 to 5 carbon atoms;
n is 0 to 4;
y is 0 or 1;
m is from 0 to 2;
M is selected from the group consisting of hydrogen and a cation;
Ac is a saturated residue of an $\alpha,\beta$-unsaturated dicarboxylic acid of 4 or 5 carbon atoms wherein the carboxylic acid groups are on adjacent carbon atoms and the double bond is between the two carbon atoms or immediately adjacent to one of them and wherein one of the carboxylic acid groups may be neutralized with a base or esterified with an alcohol of 1–6 carbon atoms
R is an alkyl of alkenyl group of 5–25 carbon atoms and each $R_1$ is alkylene of 2–4 carbons and may be the same or different.
2. A compound according to claim 1 wherein n is 0.
3. A compund according to claim 2 wherein y is 0.
4. A compound according to claim 3 wherein R is alkyl of 5 to 25 carbon atoms;
m is 1 to 2;
$R_1$ is ethylene;
$R_3$ is an alkylene group of 1 to 4 carbon atoms;
M is Na;
and Ac is as defined above.
5. A compound according to claim 4 wherein R is undecyl
m is from 1 to 1.5
$R_3$ is methylene
and Ac is a saturated residue of an $\alpha,\beta$-unsaturated dicarboxylic acid selected from the group consisting of maleic, fumaric and itaconic acids wherein one of the carboxylic acid groups may be neutralized with a base or esterified with an alcohol of 1 to 6 carbon atoms.
6. A compound according to claim 4 wherein R is undecyl;
m is from 1 to 1.5;
$R_3$ is methylene;
and Ac is a saturated residue of acrylic acid.

* * * * *